United States Patent
Kubacki (10) Patent No.: US 12,201,538 B2
(45) Date of Patent: Jan. 21, 2025

(54) EXPANDING TIBIAL STEM

(71) Applicant: WRIGHT MEDICAL TECHNOLOGY, INC., Memphis, TN (US)

(72) Inventor: Meghan Kubacki, Cookeville, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 104 days.

(21) Appl. No.: 17/814,540

(22) Filed: Jul. 25, 2022

(65) Prior Publication Data

US 2023/0089108 A1    Mar. 23, 2023

Related U.S. Application Data

(60) Provisional application No. 63/246,478, filed on Sep. 21, 2021.

(51) Int. Cl.
  *A61F 2/66* (2006.01)
  *A61B 17/16* (2006.01)
  *A61F 2/42* (2006.01)
  *A61F 2/70* (2006.01)

(52) U.S. Cl.
  CPC ........ *A61F 2/6607* (2013.01); *A61B 17/1617* (2013.01); *A61F 2/70* (2013.01); *A61F 2002/4205* (2013.01); *A61F 2220/0033* (2013.01)

(58) Field of Classification Search
  CPC .. A61F 2/6607; A61F 2/70; A61F 2002/4205; A61F 2220/033; A61F 2/42; A61F 2/4202; A61F 2/3662; A61F 2/367; A61F 2/3859; A61F 2/389; A61B 17/1617
  See application file for complete search history.

(56) References Cited

U.S. PATENT DOCUMENTS

| | | |
|---|---|---|
| 3,839,742 A | 10/1974 | Link |
| 3,872,519 A | 3/1975 | Giannestras et al. |
| 3,886,599 A | 6/1975 | Schlein |
| 3,889,300 A | 6/1975 | Smith |
| 3,896,502 A | 7/1975 | Lennox |

(Continued)

FOREIGN PATENT DOCUMENTS

| | | |
|---|---|---|
| CA | 2836651 | 3/2016 |
| CN | 101790353 | 7/2010 |

(Continued)

OTHER PUBLICATIONS

Extended European Search Report issued in connection with corresponding European Patent Application No. 22187555.2, Jan. 23, 2023, 10 pages.

(Continued)

*Primary Examiner* — Jerrah Edwards
*Assistant Examiner* — Maximilian Tobias Spencer
(74) *Attorney, Agent, or Firm* — DUANE MORRIS LLP (57) ABSTRACT

An ankle prosthesis is provided that includes a tibial stem with a retractable member configured to be controllably movable between a retracted position and an extended position so that in the extended position the retractable member engages the surface of the bone that defines an intramedullary canal so as to enhance anchoring of the tibial stem within the tibia.

14 Claims, 8 Drawing Sheets

(56) References Cited

U.S. PATENT DOCUMENTS

| | | |
|---|---|---|
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,681,590 A | 7/1987 | Tansey |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A | 6/1998 | Sammarco |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,126,691 A * | 10/2000 | Kasra ............... A61B 17/7266 606/68 |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Pericé et al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,602,259 B1 | 8/2003 | Masini |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,914,533 B2 | 3/2011 | Nelson et al. |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,128,627 B2 | 3/2012 | Justin et al. |
| 8,167,888 B2 | 5/2012 | Steffensmeier |
| 8,172,850 B2 | 5/2012 | McMinn |
| 8,177,841 B2 | 5/2012 | Ek |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |
| 8,323,346 B2 | 12/2012 | Tepic |
| 8,337,503 B2 | 12/2012 | Lian |
| 8,361,159 B2 | 1/2013 | Ek |
| 8,430,879 B2 | 4/2013 | Stoneburner et al. |
| 8,475,463 B2 | 7/2013 | Lian |
| 8,491,596 B2 | 7/2013 | Long et al. |
| 8,579,980 B2 | 11/2013 | DeLurio et al. |
| 8,715,362 B2 | 5/2014 | Reiley et al. |
| 8,808,303 B2 | 8/2014 | Stemniski et al. |
| 8,911,444 B2 | 12/2014 | Bailey |
| 9,259,250 B2 | 2/2016 | Saravia et al. |
| 9,492,281 B2 | 11/2016 | Rouyer et al. |
| 9,629,726 B2 | 4/2017 | Reiley et al. |
| 9,629,730 B2 | 4/2017 | Reiley |
| 9,907,561 B2 | 3/2018 | Luna et al. |
| 10,034,678 B2 | 7/2018 | Park et al. |
| 10,039,558 B2 | 8/2018 | Park et al. |
| 10,149,687 B2 | 12/2018 | McGinley et al. |
| 10,182,832 B1 | 1/2019 | Saltzman et al. |
| 10,206,688 B2 | 2/2019 | Park et al. |
| 10,743,999 B2 | 8/2020 | Reiley |
| 10,940,012 B2 | 3/2021 | Sander et al. |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0193268 A1 | 9/2004 | Hazebrouck |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |

(56) References Cited

U.S. PATENT DOCUMENTS

| | | |
|---|---|---|
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043309 A1 | 2/2009 | Rasmussen |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0212138 A1 | 8/2010 | Carroll et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0071645 A1 | 3/2011 | Bojarski et al. |
| 2011/0106268 A1 | 5/2011 | Deffenbaugh et al. |
| 2011/0112542 A1 | 5/2011 | Gross |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0245835 A1 | 10/2011 | Dodd et al. |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053591 A1 | 3/2012 | Haines et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2014/0276853 A1 | 9/2014 | Long et al. |
| 2014/0309640 A1 | 10/2014 | Smith et al. |
| 2014/0336658 A1* | 11/2014 | Luna ............... A61B 17/15 606/87 |
| 2015/0045801 A1 | 2/2015 | Axelson et al. |
| 2016/0135815 A1 | 5/2016 | Loring et al. |
| 2018/0177511 A1 | 6/2018 | Luna et al. |
| 2018/0263639 A1 | 9/2018 | McGinley et al. |
| 2019/0059917 A1 | 2/2019 | Saltzman |
| 2019/0059918 A1 | 2/2019 | Saltzman et al. |
| 2019/0133612 A1 | 5/2019 | McGinley |
| 2020/0246154 A1 | 8/2020 | Nachtrab |
| 2021/0038402 A1 | 2/2021 | Lee et al. |

FOREIGN PATENT DOCUMENTS

| | | |
|---|---|---|
| DE | 202012100175 U1 | 2/2012 |
| EP | 2967697 | 4/2018 |
| EP | 3354233 | 10/2019 |
| EP | 4052683 A1 | 9/2022 |
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009143374 | 11/2009 |
| WO | WO 2009158522 | 12/2009 |
| WO | WO 2010099142 | 9/2010 |
| WO | WO 2010135156 | 11/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |
| WO | WO 2016039762 | 3/2016 |

OTHER PUBLICATIONS

Search report issued for European patent application No. 13198280 dated Feb. 5, 2014.
International Search Report for International patent application No. PCT/US2014/027448 dated Jul. 7, 2014.
International Preliminary Report on Patentability issued for International patent application No. PCT/US2014/027448, Sep. 15, 2015, 8 pages.
Partial European Search Report issued in connection with European patent application No. 14768333.8, Oct. 26, 2016, 6 pages.
Patent Examination Report No. 1 issued in connection with Australian patent application No. 2015202080, Jul. 5, 2016, 4 pages.
First Office Action issued for Japanese patent application No. 2016-117842, Sep. 12, 2017, 5 pages.
First Office Action issued in connection with corresponding Japanese Patent Application No. 2020-016447, Apr. 6, 2021, 4 pages.
Office Action in corresponding Canadian Patent Application No. 2,904,652, Jun. 2, 2020, 6 pages.
First Examination Report issued in corresponding Australian Patent Application No. 2019213412, Sep. 3, 2020, 5 pages.
First Office Action in corresponding Canadian Patent Application No. 2,904,652, Jan. 28, 2020, 5 pages.
Final Office Action issued in connection with corresponding Japanese Patent Application No. 206-502443, May 15, 2018, 3 pages.

(56) References Cited

OTHER PUBLICATIONS

Extended European Search Report issued in connection with corresponding European Patent Application No. 18160378.8, Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, Sep. 3, 2018, 3 pages.
Examination Report No. 1 issued in connection with corresponding Australian Patent Application No. 20182000073, Dec. 24, 2018, 3 pages.
First Office Action issued in connection with corresponding Japanese Patent Application No. 2018-092289, Mar. 5, 2019, 2 pages.
Extended European Search Report and Opinion in connection with European Patent Application No. 14768333.8, dated Jan. 30, 2017, 10 pages.
First Office Action issued in connection with Chinese Patent Application No. 2017800899442 dated Apr. 6, 2022, 8 pages.
International Search Report and Written Opinion issued in connection with International Patent Application No. PCT/US2021/025873, Sep. 2, 2021.
Orthopedic Designs North America, Inc., http://odi-na.com/?service=talon-distalfix-fermoral-nail-system, accessed via Internet, Jul. 22, 2022.
Arthrex, "Arthrex—Intramedullary Nails," https://ww.arthrex.com/foot-ankle/intramedullary-nails, accessed via Internet, Jul. 22, 2022.

\* cited by examiner

EXPANDING TIBIAL STEM

CROSS-REFERENCE TO RELATED APPLICATION

This application claims priority under 35 U.S.C. § 119(e) to U.S. Provisional Application No. 63/246,478, filed on Sep. 21, 2021, the entire contents of which are incorporated herein by reference.

FIELD OF THE INVENTION

The invention is related to total ankle replacement surgical procedures and devices.

BACKGROUND OF THE INVENTION

Tibia stem components help fixate implants where limited bone is available for total ankle arthroplasty. "Pistoning" or loosening of the implant often presents a long-term complication. Bone in-growth into certain implant designs can inhibit establishment of replacement prostheses. Thus, improved tibial stem components that can better engage with the tibia bone, improve immediate implant stability, reduce implant migration over time, and be more easily replaced are desired.

SUMMARY OF THE INVENTION

To overcome the problems described above, preferred embodiments of the invention provide an implant that engages cancellous, and possibly cortical, tibia bone to improve immediate implant stability and reduce implant migration long term. Retractable members are movable from a withdrawn position to extend outward and retractable to be fully captured within the device.

According to one embodiment of the invention, an ankle prosthesis incorporates a tibial stem including a leading end, a trailing end, and a longitudinal axis defined therethrough. A tibia tray is provided and configured to be attached to a prosthetic joint articulating surface, where the tibia tray extends from the trailing end and is sized and configured to be placed in a resected tibia or, in some embodiments, a resected joint. The tibial stem is configured to be placed in an intramedullary canal defined in a tibia, and includes a retractable member configured to be controllably movable between (i) a retracted position and (ii) an outwardly, longitudinally extended position to a deployed position. In the retracted position, the retractable member is contained substantially within the tibial stem and does not extend outwardly. The retractable member is able to engage the bone that defines the intramedullary canal within the tibia thereby to enhance anchoring of the tibial stem within the intramedullary canal when the tibial stem is located in the intramedullary canal and the retractable member is in the deployed position. Often, the retractable member is configured to be moved back to the retracted position from the deployed position. Additionally, the tibia tray often includes a channel extending between a pair of opposed rails to receive a prosthetic joint surface. In some embodiments, the channel extends in at least one of an anterior-posterior direction, a medial-lateral direction, and in an oblique direction. In other embodiments, the tibial stem may include an elongated, generally cylindrical shell that defines an internal cavity that is open at the trailing end. In many embodiments, there is formed an opening in the cylindrical shell through which the retractable member may move between the retracted position and the deployed position.

In another embodiment of the invention, the tibial stem further includes a rotational actuator, located within the internal cavity, that is configured to rotate within the internal cavity around a longitudinal axis. The retractable member may include an engagement end, teeth, and a tail end. The engagement end is often a free end that is movable through the opening provided in the cylindrical shell of the tibial stem so as to engage the internal surface of the tibia that defines the intramedullary canal. Here, the retractable member may be located between (i) a retracted position and (ii) a deployed position, by rotating the rotational actuator within the internal cavity. Often, the rotational actuator includes a tool interface to receive a tool used to rotate the rotational actuator, where the tool interface may be accessed in a channel of the tibia tray that extends between a pair of opposed rails that arranged so as to receive the prosthetic joint surface. Also, the rotational actuator may include a gear portion that meshes with the teeth of the retractable member so that by rotating the rotational actuator the gear portion rotates and moves the retractable member. The prosthesis of the invention often further includes a coating or surface modification on the tibial stem and/or the tibia tray to promote bony in-growth.

The above and other features, elements, characteristics, steps, and advantages of the invention will become more apparent from the following detailed description of preferred embodiments of the invention with reference to the attached drawings.

BRIEF DESCRIPTION OF DRAWINGS

The features of the embodiments described herein will be more fully disclosed in the following detailed description, which is to be considered together with the accompanying drawings wherein like numbers refer to like parts.

DETAILED DESCRIPTION OF PREFERRED EMBODIMENTS

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The methods, systems, and structures described for the ankle herein may be adapted to other applications in arthroplasty, including but not limited to the knee, shoulder, hip, elbow, and other joints.

Figure 1:
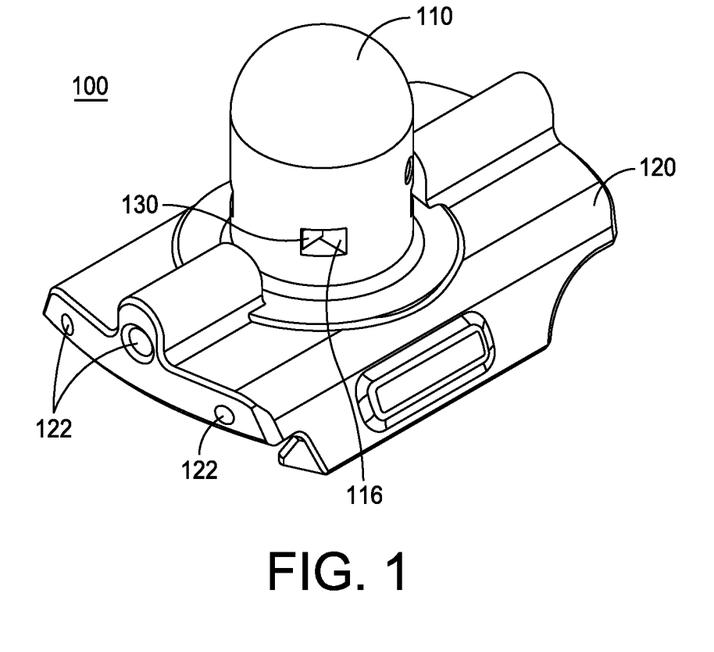
FIGS. 1 and 2 are illustrations of a prosthesis formed in accordance to one embodiment of the invention.
Figure 2:
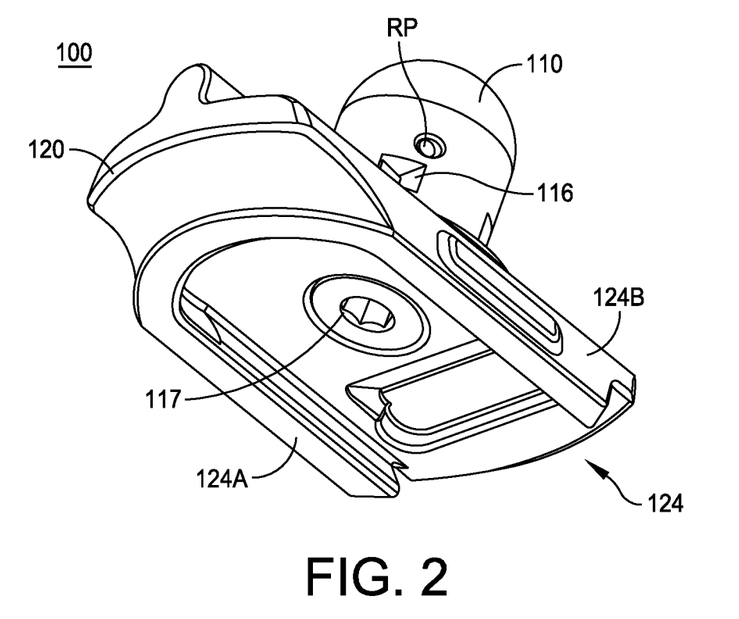
Figure 3:
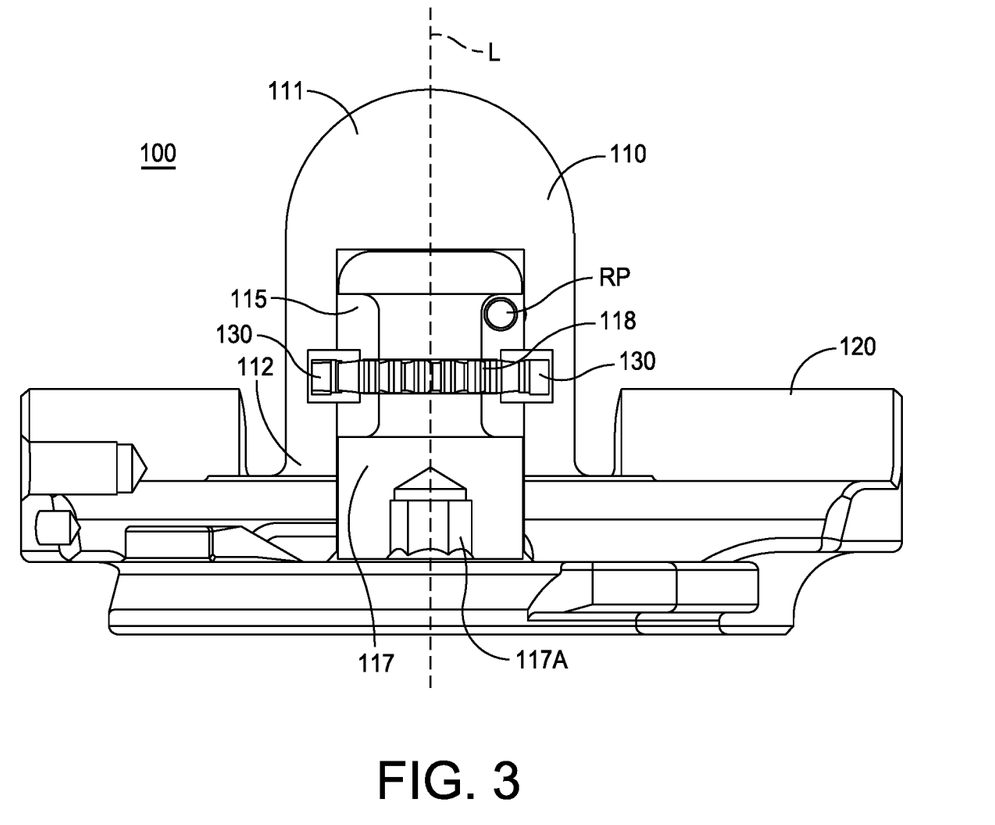
FIG. 3 is a cross section view of the prosthesis formed in accordance to one embodiment of the invention.

Referring to FIGS. 1-5, an ankle prosthesis 100 according to an embodiment of the invention includes a tibial stem 110 and a tibia tray 120 configured to be attached to a prosthetic joint articulating surface. Optionally, the ankle prosthesis 100 may be fabricated such that the tibial stem 110 and the tibia tray 120 are monolithic, e.g., made integral with one another as one piece. As shown in FIG. 3, the tibial stem 110 may include a leading end 111, a trailing end 112, and a longitudinal axis L.

The tibia tray 120 extends from the trailing end 112 of the tibial stem 110. The tibial stem 110 may be sized and configured to be inserted in an intramedullary canal defined by the interior bone surface of a tibia. The tibial stem 110 may include one or more retractable members 130 configured to be controllably movable between a retracted position and an outwardly extended position that is away from the tibial stem 110 so as to in a deployed or extended position. In the retracted position, the one or more retractable members 130 may be contained within the envelope of the tibial stem 110 and do not extend outside of openings 116 in the tibial stem 110. In use, after the tibial stem 110 has been placed within the intramedullary canal of a tibia, the one or more retractable members 130 may be moved from their retracted position outwardly and away from the longitudinal axis L so that the one or more retractable members 130 engage the surface of the bone defining the intramedullary canal's so as to enhance anchoring of the tibial stem 110 within the tibia. Referring to FIG. 1, the tibia tray 120 may also include a tooling interface 122 that may be used to fit tools used to handle, place, locate, or replace the ankle prosthesis 100 during surgery. As shown, the tooling interface 122 may include circular recesses in a side of the tibia tray 120. Optionally, the tooling interface 122 may be threaded or tapered, and may be any suitable shape.

The tibial stem 110 may include one or more retractable members 130 (shown as two in the figures). In many situations, having two retractable members 130 may provide anchoring configurations that are more symmetrical. The symmetry involved here may be planar symmetry or radial symmetry with respect to the longitudinal axis L of the tibial stem 110. Retraction of the retractable members 130 allows for in-situ installation, adjustment, repositioning, and removal of the tibial stem 110 as required by the surgeon. Referring to FIG. 2, the tibia tray 120 may include a channel 124 extending between a pair of opposed rails 124A and 124B so as to receive a prosthetic joint surface. The channel 124 in the tibia tray 120 may extend in at least one of an anterior-posterior direction, medial-lateral direction, and in an oblique direction.

Figure 4:
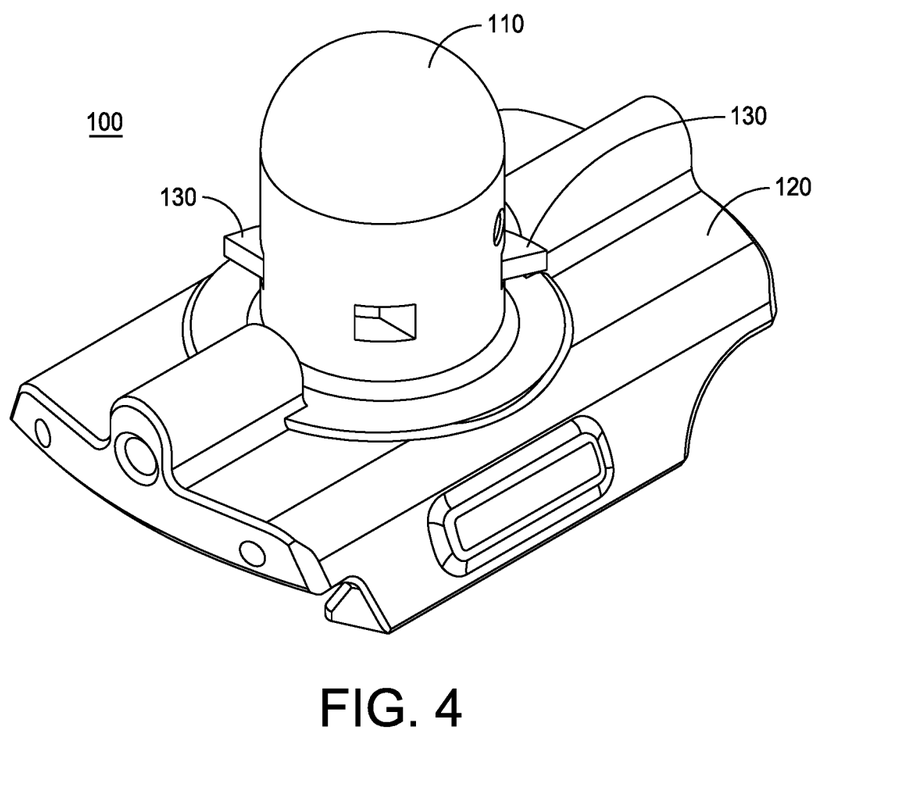
FIGS. 4 and 5 are illustrations of the prosthesis with deployed retractable members formed in accordance to one embodiment of the invention.
Figure 5:
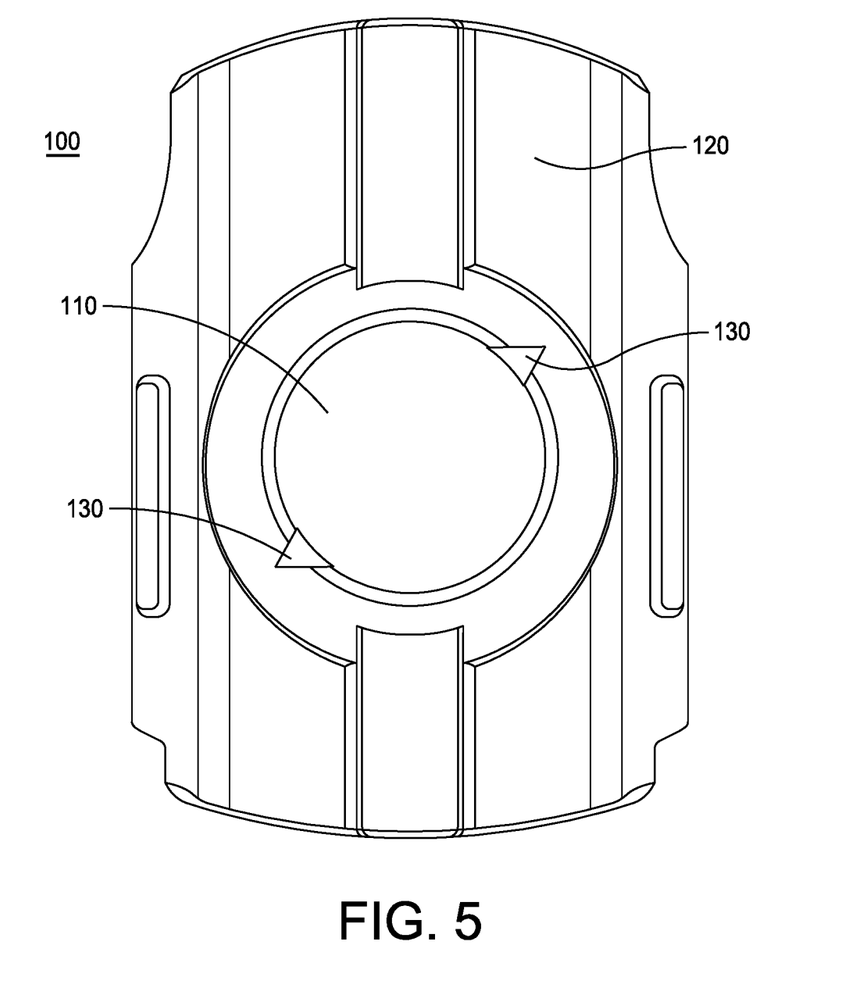

Referring to FIGS. 4 and 5, the retractable members 130 extend away from the longitudinal axis L of the tibial stem 110 when moving from their retracted positions outwardly and away from the longitudinal axis L to the deployed position. The one or more retractable members 130 may retract toward the longitudinal axis L of the tibial stem 110 when moving from their deployed positions to their retracted positions. The tibial stem 110 may include an elongated generally cylindrical shell defining an internal cavity 115 that is open at the trailing end 112. An opening 116 is provided in the generally cylindrical shell of the tibial stem 110 for each of the retractable members 130. The retractable members 130 extend outward through the openings 116 from the retracted position. The in and out movements of the retractable members 130 allow for suitable anchoring and eases release of the tibial stem 110 during relocation or replacement of the prosthesis 100. Although, the shape of the shell forming the tibial stem 110 is referred to as being generally cylindrical, the invention encompasses a variety of shapes for the shell other than those having circular or oval cross-sections. The term "generally cylindrical" as used herein is intended to encompass a structure for the shell that may have a variety of other cross-sectional shapes such as polygons (i.e., a triangle, a quadrilateral, a pentagon, a hexagon, a heptagon, a cone, an octagon, etc.). Additionally, the term "generally cylindrical" as used herein is intended to encompass structures that may not have a continuous solid shell.

Figure 6:
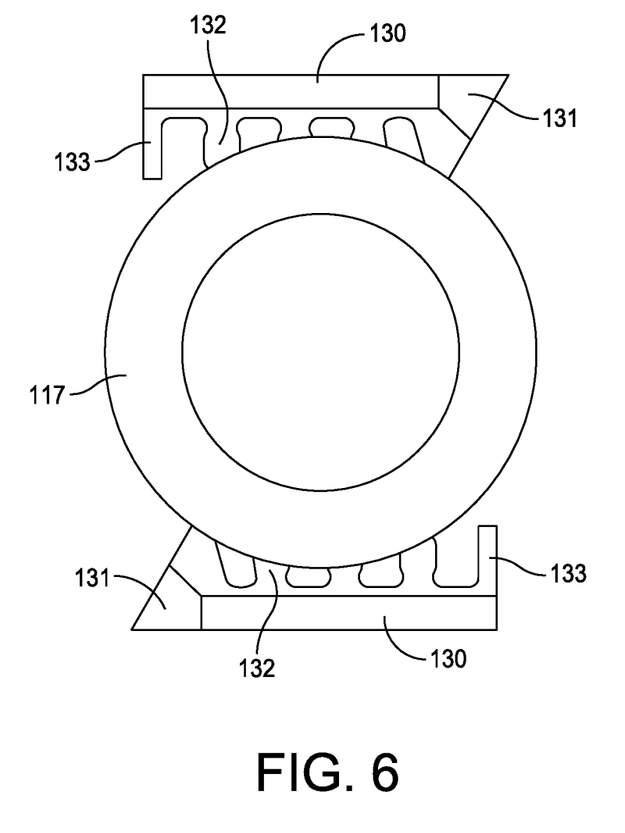
FIG. 6 is a top view of the actuation assembly of the prosthesis formed in accordance to one embodiment of the invention.

As best viewed in FIG. 3, the tibial stem 110 may further include a rotational actuator 117 provided within the internal cavity 115. The rotational actuator 117 is configured to rotate within the internal cavity 115 around the longitudinal axis L. Referring to FIG. 6, each of the retractable members 130 may include an engagement end 131, teeth 132, and a tail end 133. The teeth 132 are engaged with a gear portion 118 of the rotational actuator 117. The engagement end 131 is a free end that is movable through its respective opening 116 to engage the bone surface, that defines the intramedullary canal, as the prosthesis 100 is installed inside the intramedullary canal of a tibia. The gear portion 118 may include a circular gear including teeth to match the teeth 132 of the retractable members 130. The movement of the retractable members 130 from the retracted position to the deployed position is controllably achieved by rotating the rotational actuator 117 within the internal cavity 115. The movement of the rotational actuator 117 may be either clockwise or counter-clockwise around the longitudinal axis L.

The rotational movement of the rotational actuator 117 may be controlled by providing a tool interface. By way of example, the base of the rotational actuator 117 may be provided with a tool-receiving socket 117A (See FIGS. 2 and 3) at the bottom end so that a tool, e.g., a wrench or a screwdriver, may be used to turn the rotational actuator 117 and control the movement of the retractable members 130. To limit over rotation of the rotational actuator 117, the tail end 133 of the retractable members 130 may include a flat feature (shown in FIG. 6) that is not a tooth to cause interference between the retractable members 130 and the rotational actuator 117 when the tail end 133 engages with the rotational actuator 117.

Figure 7:
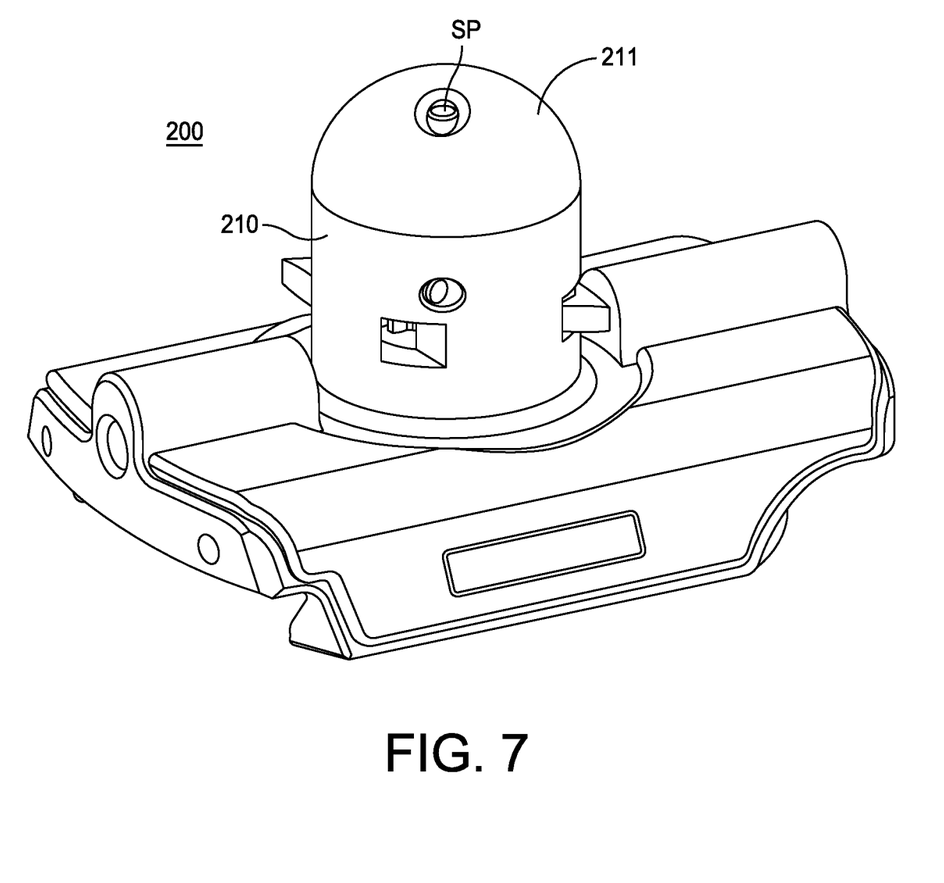
FIG. 7-9 are illustrations of another prosthesis formed in accordance to one embodiment of the invention.
Figure 8:
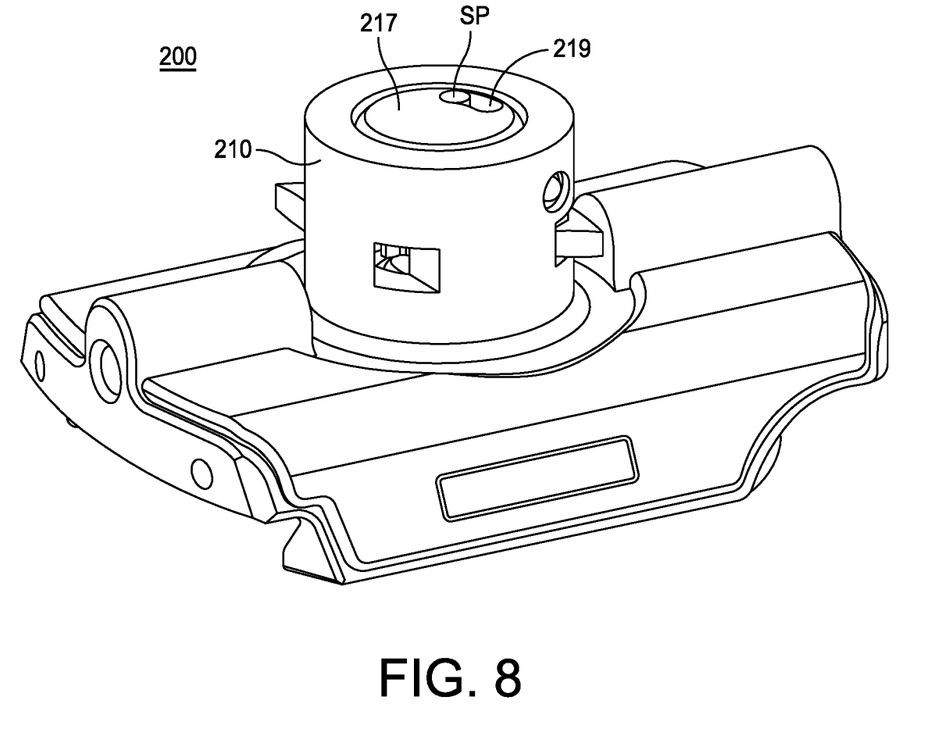
Figure 9:
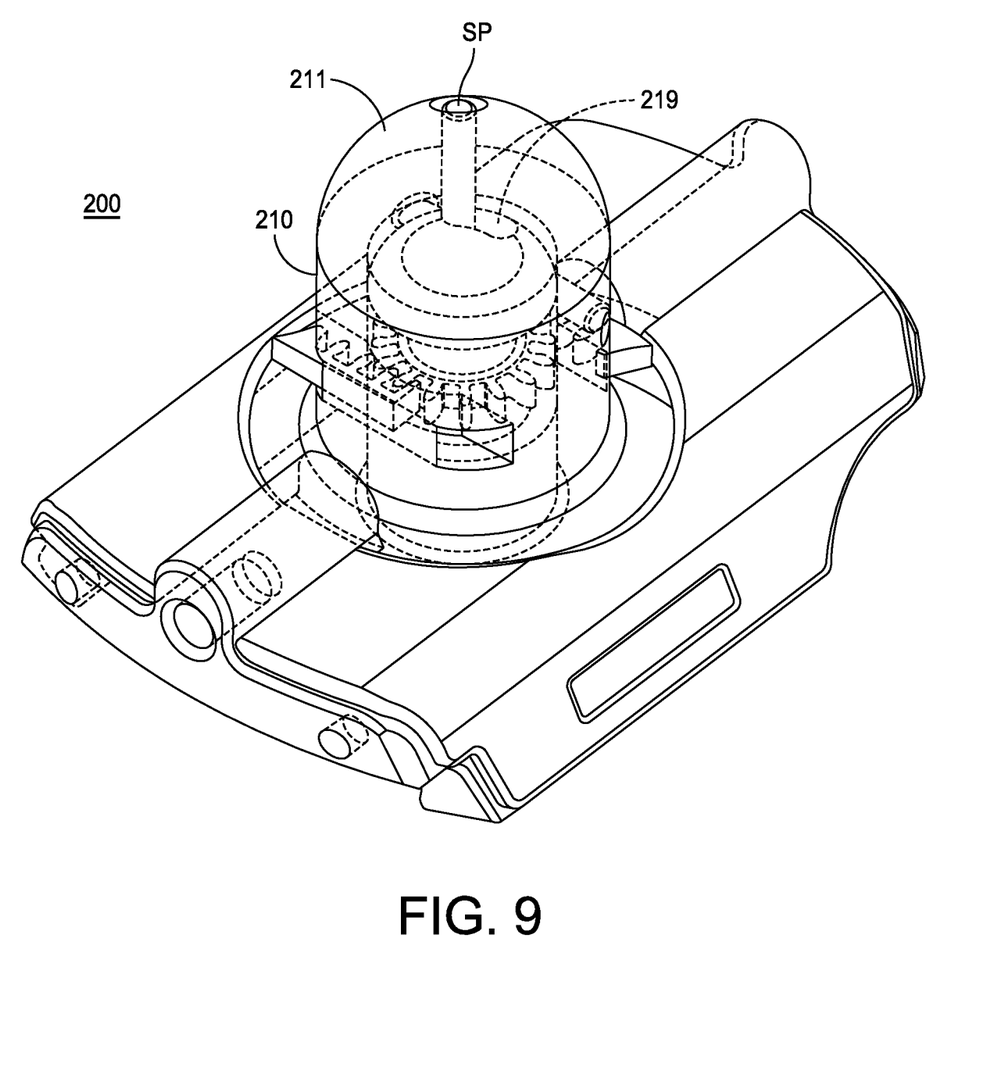

Referring to FIGS. 7-9, an ankle prosthesis 200 formed in accordance with another embodiment includes a groove 219 that may be defined in the mushroom-shaped top of a rotational actuator 217 and a pin SP may be inserted in the leading end 211 of the tibial stem 210 and into the groove 219 so that there is a hard-stop to prevent rotation of the rotational actuator 217 once the retractable members 130 reach the deployed position. FIG. 8 is a section view where the leading end 211 has been removed so the groove 219 is visible. FIG. 9 is a view with the leading end 211 and the tibial stem 210 transparent so that the groove 219 and pin SP are visible.

Referring again to FIG. 3, in another embodiment of the invention the rotational actuator 117 may be retained within the cavity 115 using a retaining pin RP. The tibial stem 110 may define a through-hole to receive the retaining pin RP. The through-hole is positioned such that the retaining pin RP extends through the through-hole of the tibial stem 110 and is aligned to fit under a mushroom-shaped top of the rotational actuator 117, as shown in the cross-sectional view of FIG. 3. In other embodiments, more than one retaining pin RP may be used to retain the rotational actuator 117. The tibial stem 110 may be made of a shape memory alloy such as Nitinol so that the super elastic properties or the memory properties of such alloy may be employed to enhance the function of the retractable members 130.

In further embodiments, the tibial stem 110 and/or the tibia tray 120 may be made of any material commonly used in the prosthetic arts, including, but not limited to, metals, ceramics, titanium, titanium alloys, tantalum, chrome cobalt, surgical steel, polyethylene, absorbable polymer, or any other total joint replacement metal and/or ceramic via traditional subtractive manufacturing or additive manufacturing techniques. In some embodiments, the tibial stem 110 and/or the tibia tray 120 may include a coating of Biofoam™, Adaptis™, porous metal, sintered glass, artificial bone, any uncemented metal or ceramic surface, or a combination thereof that would promote bony in-growth. The tibial stem 110 and/or the tibia tray 120 may further be covered with one or more coatings, such as, antimicrobial, antithrombotic, and osteoinductive agents, or a combination thereof. In some embodiments where the above-mentioned porous coating is provided, these agents may further be carried in a biodegradable carrier material with which the pores in the porous coating may be impregnated.

It should be understood that the foregoing description is only illustrative of the invention. Various alternatives and modifications may be devised by those skilled in the art without departing from the scope of the invention. Accordingly, the invention is intended to embrace all such alternatives, modifications, and variances that fall within the scope of the appended claims.

What is claimed is:

1. A prosthesis, comprising:
   a stem including a leading end, a trailing end, a longitudinal axis, and a rotational actuator including a tool-receiving socket defined at a first end and located within an internal cavity defined by an elongate hollow shell that is open at the trailing end with an opening defined in the shell through which a retractable member can move between a retracted position within the hollow shell and a deployed position by rotation of the tool-receiving socket, the internal cavity having an open end, a rotational actuator being configured with a circular gear including gear teeth and arranged so as to rotate within the internal cavity and about the longitudinal axis and coupled to the retractable member, which includes an engagement end, member teeth operatively engageable with the gear teeth, and a flat tail end, such that the engagement end is movable through the opening defined in the cylindrical shell so that rotating the rotational actuator while engaging the tool-receiving socket, urges the member teeth to operatively engage the gear teeth so that the retractable member is moved outwardly from the retracted position to the deployed position determined by the engagement of the flat tail end with the gear teeth so as to effect deployment of the retractable member into engagement with a bone; and
   a tray extending from the trailing end configured to be attached to a prosthetic joint articulating surface and sized and configured to be placed in a resected joint, the tray defining a central opening that is positioned between a pair of opposed rails and in aligned communication with the tool-receiving socket when attached to the prosthetic joint so that the tool-receiving socket (i) causes the rotation of the rotational actuator within the internal cavity when rotationally engaged by a tool and (ii) is covered by a portion of the prosthetic joint articulating surface upon deployment of the retractable member through the open end.

2. The ankle prosthesis of claim 1, wherein the rotational actuator includes a gear portion that meshes with the teeth of the retractable member, and rotating the rotational actuator rotates the gear portion and moves the retractable member.

3. An ankle prosthesis, comprising:
   a tibial stem including a leading end, a trailing end, an internal cavity defined by an elongate hollow shell that is open at the trailing end with an opening defined through the shell, a longitudinal axis, and a rotational actuator configured with a circular gear including gear teeth arranged so as to rotate within the internal cavity and about the longitudinal axis of the tibial stem;
   a tibia tray configured to be attached to a prosthetic joint articulating surface, wherein
   the tibia tray defines a central opening between a pair of opposed rails and extends from the trailing end and is sized and configured to be placed in a resected tibia;
   the tibial stem is configured to be placed in a tibial intramedullary canal, and includes a retractable member having an engagement end, member teeth operatively engageable with the gear teeth, and a flat tail end, such that the engagement end is movable through the opening defined in the hollow shell, and having a tool-receiving socket defined at a first end and configured to be located with the internal cavity in communication with the central opening of the tibia tray so as to provide controlled rotational movement between (i) a retracted position and (ii) a deployed position by rotating the rotational actuator within the internal cavity so that the member teeth operatively engage the gear teeth thereby urging the retractable member to move outwardly and away from the longitudinal axis of the tibial stem such that in the retracted position the retractable member is contained substantially within the tibial stem, when in the deployed position the engagement end of the retractable member engages the bone surface that defines the intramedullary canal as the flat tail end of the retractable member engages the gear teeth thereby anchoring the tibial stem within the tibia; and
- a prosthetic joint articulating surface coupled to the tibia tray so as to cover the tool-receiving socket.

4. The ankle prosthesis of claim 3, wherein the retractable member is configured to be moved back to the retracted position from the deployed position when the tool-receiving socket is uncovered.

5. The ankle prosthesis of claim 3, wherein the tibia tray includes a channel extending between the pair of opposed rails to receive the prosthetic joint articulating surface.

6. The ankle prosthesis of claim 5, wherein the channel extends in at least one of an anterior-posterior direction, a medial-lateral direction, and in an oblique direction.

7. The ankle prosthesis of claim 3, wherein the tool-receiving socket is accessed in a channel of the tibia tray that extends between a pair of opposed rails to receive the prosthetic joint surface.

8. The ankle prosthesis of claim 3, further comprising a coating on the tibial stem and/or the tibia tray to promote bony in-growth.

9. An ankle prosthesis, comprising:
- a tibial stem including a leading end, a trailing end, a longitudinal axis, and an actuator located within an internal cavity defined by an elongate hollow shell that is open at the trailing end with an opening defined through the shell, the internal cavity having an open end, the actuator including a tool interface and a circular gear including gear teeth arranged so as to rotate within the internal cavity so as to be configured to move within the internal cavity and about the longitudinal axis of the tibial stem and coupled to a retractable member having an engagement end, member teeth operatively engageable with the gear teeth, and a flat tail end, such that the engagement end is movable through the opening defined in the hollow shell so as to thereby effect deployment of the retractable member through the opening in the hollow shell and away from the longitudinal axis of the tibial stem by rotation of the tool interface determined by the engagement of the gear teeth with the flat tail end; and
- a tibia tray extending from the trailing end configured to be attached to a prosthetic joint articulating surface and sized and configured to cover the tool interface when placed in a resected tibia.

10. The ankle prosthesis of claim 9, wherein the retractable member is configured to be controllably movable by the actuator between (i) a retracted position and (ii) a deployed position that is outward and away from the longitudinal axis.

11. The ankle prosthesis of claim 10, wherein in the retracted position the retractable member is contained substantially within internal cavity and when in the deployed position the retractable member extends from the internal cavity so as to engage the bone surface that defines the intramedullary canal thereby anchoring the tibial stem within the tibia.

12. The ankle prosthesis of claim 10, wherein the retractable member is configured to be moved back to the retracted position from the deployed position when the tool interface is uncovered.

13. The ankle prosthesis of claim 10, wherein the tibia tray includes a channel extending between a pair of opposed rails to receive the prosthetic joint articulating surface.

14. The ankle prosthesis of claim 13, wherein the channel extends in at least one of an anterior-posterior direction, a medial-lateral direction, and in an oblique direction.

\* \* \* \* \*